United States Patent [19]

Kunz et al.

[11] Patent Number: 5,066,661
[45] Date of Patent: Nov. 19, 1991

[54] AGENTS FOR PROTECTING PLANTS AGAINST DISEASES

[75] Inventors: Walter Kunz, Oberwil; Rolf Schurter, Binningen; Robert Nyfeler, Basle, all of Switzerland

[73] Assignee: Ciba-Geigy Corporation, Ardsley, N.Y.

[21] Appl. No.: 489,414

[22] Filed: Mar. 6, 1990

[30] Foreign Application Priority Data

Mar. 8, 1989 [CH] Switzerland ............... 864/89

[51] Int. Cl.⁵ .................. C07D 285/14; A01N 43/82
[52] U.S. Cl. ........................... 514/361; 548/126
[58] Field of Search ................. 548/126; 514/361

[56] References Cited

U.S. PATENT DOCUMENTS 4,931,581  6/1990  Schurter ................ 560/18

Primary Examiner—Robert Gerstl
Attorney, Agent, or Firm—George R. Dohmann; Edward McC. Roberts

[57] ABSTRACT

The invention relates to novel N-(cyanomethyl)-benzo-1,2,3-thiadiazole-7-carboxamides of the formula I

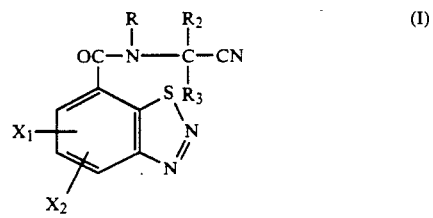

in which $X_1$ and $X_2$ independently of one another are hydrogen or 1 to 3 halogen; R is hydrogen $C_1$-$C_4$alkyl, $C_3$-$C_5$alkenyl or $SR_1$; $R_1$ is $C_1$-$C_3$alkyl which is substituted by 3 to 6 fluorine or chlorine; $R_2$ is $C_1$-$C_4$alkyl, or is $C_1$-$C_5$alkyl which is interrupted by oxygen, or is $C_1$-$C_6$alkoxy, or is $C_1$-$C_3$alkyl which is substituted by 1 to 3 halogen, or is substituted $C_2$-$C_3$alkoxy, or is $C_1$-$C_6$alkylthio, or is furyl or thienyl, each of which is bonded in the 2- or 3-position, or is furyl or thienyl, each of which is substituted by 1 to 3 halogen and bonded in the 2- or 3-position; and $R_3$ is hydrogen or $C_1$-$C_4$alkyl.

Such compounds, by themselves or in the form of formulated agents, can be used for protecting plants against harmful microorganisms.

17 Claims, No Drawings

AGENTS FOR PROTECTING PLANTS AGAINST DISEASES

The present invention relates to novel N-(cyanomethyl)-benz-1,2,3-thiadiazole-7-carboxamides of the formula I below. The invention furthermore relates to the preparation of these substances and to the agents containing at least one of these compounds as active ingredient. Moreover, the invention relates to the preparation of the abovementioned agents and to the use of the active ingredients or of the agents for protecting plants against attack by harmful microorganisms, for example phytopathogenic fungi, bacteria and viruses.

The compounds according to the invention correspond to the general formula I

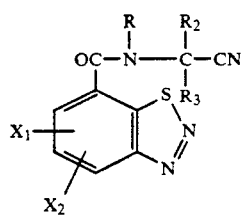

in which $X_1$ and $X_2$ independently of one another are hydrogen or 1 to 3 halogen; R is hydrogen, $C_1$-$C_4$alkyl, $C_3$-$C_5$alkenyl or $SR_1$; $R_1$ is $C_1$-$C_3$alkyl which is substituted by 3 to 6 fluorine or chlorine; $R_2$ is $C_1$-$C_4$alkyl, or is $C_1$-$C_5$alkyl which is interrupted by oxygen, or is $C_1$-$C_6$alkoxy, or is $C_1$-$C_3$alkyl which is substituted by 1 to 3 halogen, or is substituted $C_2$-$C_3$alkoxy, or is $C_1$-$C_6$alkylthio, or is furyl or thienyl, each of which is bonded in the 2- or 3-position, or is furyl or thienyl, each of which is substituted by 1 to 3 halogen and bonded in the 2- or 3-position; and $R_3$ is hydrogen or $C_1$-$C_4$alkyl.

Halogen is fluorine, chlorine, bromine or iodine, preferably fluorine and furthermore in the sequence chlorine, bromine and iodine. As substituent in individual radicals, halogen can be present 1 to 3 times.

Alkyl itself or as a constituent of another substituent is to be understood as meaning straight-chain and branched alkyls. Depending on the number of the carbon atoms indicated, they represent, for example, the following groups: methyl, ethyl and the isomers of propyl or butyl, for example isopropyl, isobutyl, tert-butyl or sec-butyl.

Alkenyl for example represents propen-1-yl, allyl, buten-1-yl, buten-2-yl or buten-3-yl.

In particular, the invention relates to compounds of the formula I in which: $X_1$ and $X_2$ independently of one another are hydrogen or 1 or 2 or together not more than 3 fluorine; R is hydrogen, methyl, ethyl, allyl or the radical S—$R_1$; $R_1$ is trichloromethyl, dichlorofluoromethyl or 1,1,2,2-tetrachloroethyl.

Other preferred compounds of the formula I are those in which: $X_1$ and $X_2$ independently of one another are hydrogen or fluorine; R is hydrogen; $R_2$ is $C_1$-$C_4$alkoxy, $C_1$-$C_4$alkylthio, or is furyl or thienyl, each of which is bonded in the 2- or 3-position, or is furyl or thienyl, each of which is substituted by 1 to 3 halogen and bonded in the 2- or 3-position; and $R_3$ is hydrogen or $C_1$-$C_3$alkyl.

On the basis of their particular plant-protecting properties, the compounds of the formula I can be divided into the following groups:

1. Compounds of the formula I where: $X_1$ and $X_2$ independently of one another are hydrogen or fluorine; R is hydrogen, methyl, ethyl, allyl or the radical S—$R_1$; $R_1$ is trichloromethyl, dichlorofluoromethyl or 1,1,2,2-tetrachloroethyl; $R_2$ is $C_1$-$C_4$alkyl, or $C_1$-$C_5$alkyl which is interrupted by oxygen, or $C_1$-$C_6$alkoxy, trichloromethyl, trifluoromethyl, 1,1,1-trifluoroethoxy, $C_1$-$C_6$alkylthio, or is furyl or thienyl, each of which is bonded in the 2- or 3-position, or is furyl or thienyl, each of which is substituted by 1 to 3 halogen and bonded in the 2- or 3-position; and $R_3$ is hydrogen or methyl.

2. Compounds of the formula I where: $X_1$ and $X_2$ independently of one another are hydrogen or fluorine; R is hydrogen, methyl, ethyl, allyl or the radical S—$R_1$; $R_1$ is trichloromethyl, dichlorofluoromethyl or 1,1,2,2-tetrachloroethyl; $R_2$ is $C_1$-$C_4$alkyl, or is $C_1$-$C_5$alkyl which is interrupted by oxygen, or is $C_1$-$C_6$alkoxy, trichloromethyl, trifluoromethyl, 1,1,1-trifluoroethoxy, $C_1$-$C_6$alkylthio, or is furyl or thienyl, each of which is bonded in the 2- or 3-position, or is furyl or thienyl, each of which is substituted by 1 to 3 halogen and bonded in the 2-or 3-position; and $R_3$ is hydrogen.

3. Compounds of the formula I where: $X_1$ and $X_2$ independently of one another are hydrogen or fluorine; R is hydrogen; $R_2$ is $C_1$-$C_6$alkoxy, $C_1$-$C_6$alkylthio, or is furyl or thienyl, each of which is bonded in the 2- or 3-position; and $R_3$ is hydrogen.

The following compounds are distinguished by particularly advantageous plant-protecting properties:

N-(benzo-1,2,3-thiadiazole-7-carbonyl)-2-ethoxy-2-aminoacetonitrile;

N-(benzo-1,2,3-thiadiazole-7-carbonyl)-2-methoxy-2-aminoacetonitrile;

N-(benzo-1,2,3-thiadiazole-7-carbonyl)-2-(furyl-2'yl)-2-aminoacetonitrile;

N-(benzo-1,2,3-thiadiazole-7-carbonyl)-2-(thiophen-2'yl)-2-aminoacetonitrile;

N-(benzo-1,2,3-thiadiazole-7-carbonyl)-2-(thiophen-3'yl)-2-aminoacetonitrile;

N-(5-fluorobenzo-1,2,3-thiadiazole-7-carbonyl)-2-(thiophen-3'yl)-2-aminoacetonitrile;

N-(4-fluorobenzo-1,2,3-thiadiazole-7-carbonyl)-2-(thiophen-3'yl)-2-aminoacetonitrile;

N-(benzo-1,2,3-thiadiazole-7-carbonyl)-2-(furyl-3'yl)-2-aminoacetonitrile;

N-(benzo-1,2,3-thiadiazole-7-carbonyl)-2-methylthio-2-aminoacetonitrile;

N-(benzo-1,2,3-thiadiazole-7-carbonyl)-2-isopropylthio-2-aminoacetonitrile.

Surprisingly, it has now been found that use of the compounds of the formula I according to the invention inhibits plants from being attacked by harmful microorganisms and therefore prevents damage of the plants caused by attack. It is characteristic of the active ingredients according to the invention that the protection of the plants can be achieved either by direct action on the phytopathogenic microorganisms by means of foliar application or by means of soil application, or by activation or stimulation of the plants' intrinsic defence system (immunization). The big advantage of the compounds of the formula I is the fact that it can be ensured that the plants treated with these substances remain healthy during the vegetation period by themselves, without further microbicidal substances being used.

Accordingly, it is possible, by using the active ingredients according to the invention, to avoid disadvantageous side effects, as can occur in the direct control of parasites by chemical substances, for example, on the one hand, by damaging the crop plants (phytotoxicity) and, on the other hand, by causing signs of resistance in the harmful microorganisms, which, advantageously, results in an entirely undisturbed growth of the crop plants.

Broad-range protection of the plants against diseases can be achieved by virtue of the two-fold mechanism of action of the compounds of the formula I according to the invention, namely, on the one hand, direct control of the phytopathogens and, on the other hand, increasing the general readiness for defence of the plants treated with these active ingredients. The use of the active ingredients according to the invention is therefore particularly suitable for practice conditions. Moreover, the systemic activity which is characteristic of the compounds of the formula I has the effect that the protective action also extends as far as the additional growth of the treated plants.

The general plant-protecting activity of the active ingredients according to the invention is active, for example, against the phytopathogenic fungi of the following classes: Fungi imperfecti (for example Botrytis, Helminthosporium, Fusarium, Septoria, Cercospora and Alternaria); Basidiomycetes (for example the genera Hemileia, Rhizocotonia, Puccinia); Ascomycetes (for example Venturia, Podosphaera, Erysiphe, Monilinia, Uncinula).

Moreover, the active ingredients can be used particularly advantageously against the following harmful organisms: fungi, for example Oomycetes (for example *Plasmopara viticola, Phytophthora infestans, Peronospora tabacina*, Pseudoperonospora, Bremia letucae), *Fungi imperfecti* (for example *Colletotrichum lagenarium, Pyricularia oryzae, Cercospora nicotinae*), Ascomycetes (for example *Venturia inaequalis*); bacteria, for example Pseudomonadaceae (*Pseudomonas lachrymans, Pseudomonas tomato, Pseudomonas tabaci*); Xanthomonadaceae (for example *Xanthomonas oryzae, Xanthomonas vesicatoria*); Erwinia (for example *Erwinia amylovora*); and viruses, for example tobacco mosaic virus.

The compounds according to the invention can be used for protecting plants of various crops.

Examples of plant species which are suitable for the use of the compounds of the formula I according to the invention within the scope of the invention are the following: cereals (wheat, barley, rye, oats, rice, sorghum and related species); beets (sugar beet and fodder beet); pomaceous fruit, stone fruit and soft fruit (apples, pairs, plums, peaches, almonds, cherries, strawberries, raspberries and blackberries); pulses (beans, lentils, peas, soybeans); oil crops (oilseed rape, mustard, poppy, olives, sunflowers, coconut, castor, cacao, groundnuts); members of the gourd family (pumpkin, cucumbers, melons); fibre plants (cotton, flax, hemp, jute); citrus fruits (oranges, lemons, grapefruit, tangerines); various vegetables (spinach, lettuce, asparagus, cabbage species, carrots, onions, tomatoes, potatoes, capsicums); Lauraceae (avocado, Cinnamonum, camphor), or plants such as maize, tobacco, nuts, coffee, sugar cane, tea, grapevines, hops, Musaceae and rubber plants, and also ornamental plants (flowers, shrubs, deciduous trees and conifers). This enumeration is non-limiting.

The following plants are to be considered as particularly suitable target crops for the use of the process according to the invention: cucumbers, tobacco, vines, rice, pepper, potatoes, tomatoes, wheat, barley, pears and apples.

Compounds of the formula I with the exception of those compounds in which R is the radical S—R$_1$ and R$_2$ is C$_1$-C$_6$alkoxy or C$_1$-C$_6$alkylthio are prepared by reacting: a benzothiadiazole compound of the formula II

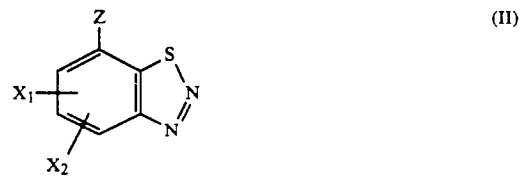

with an amino compound of the formula III

in the presence of a base and if appropriate with a catalyst, for example 4-dialkylaminopyridine, specifically 4-dimethylaminopyridine, in inert solvents, where Z is the radicals COOH, Hal—CO, COOC$_1$-C$_5$alkyl,

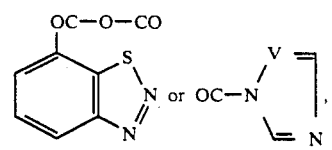

V is CH or N and Hal is halogen and R' has the meaning of R as in formula I with the exception of S—R$_1$, and R$_2$' has the meaning of R$_2$ as in formula I, with the exception of C$_1$-C$_6$alkoxy or C$_1$-C$_6$alkylthio, and X$_1$, X$_2$ and R$_3$ have the meanings indicated in the case of formula I. The reaction is effected at temperatures of from −10° to 160° C., preferably from 0° C. to 100° C.

Compounds of the formula I in which the meaning S—R$_1$ is excluded for R (=R') and in which R$_2$ is C$_1$-C$_6$alkoxy or C$_1$-C$_6$alkylthio (=R$_2$") are prepared by:

a) reacting a benzothiadiazole compound of the formula II

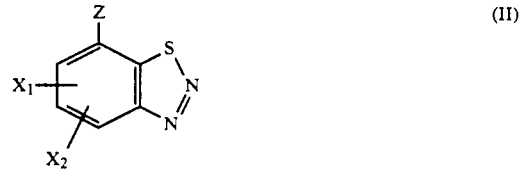

with an amino compound of the formula III'

in the presence of a base in inert solvents at temperatures of from −10° to 160° C., preferably from 0° C. to 100° C., to give an amide compound of the formula IV

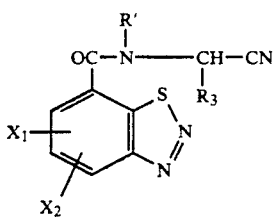
(IV)

and subsequently b) converting the compound of the formula IV into a halogen compound of the formula V

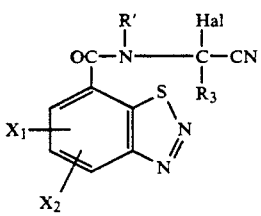
(V)

with a halogenating agent in inert solvents at temperatures of from −30° to 70° C., preferably from 0° to 40° C., and then c) etherifying the compound of the formula V, after isolation or without isolation, with an alcohol or thiol of the formula VI $HR_2''$ (VI)

in the presence of a base in inert solvents at temperatures of from −20° to 160° C., preferably from 0° to 100° C., where Z is the radicals COOH, Hal—CO, $COOC_1-C_3$alkyl,

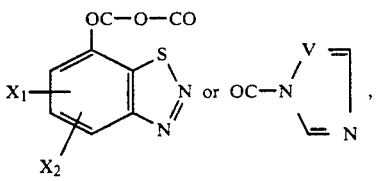

V is CH or N and Hal is halogen, and R′ has the meaning of R as in formula I with the exception of S—$R_1$, and $R_2''$ has the meaning of $C_1-C_6$alkoxy and $C_1-C_6$alkylthio, and $X_1$, $X_2$ and $R_3$ have the meanings indicated in the case of formula I.

Compounds of the formula I in which R has the meaning of S—$R_1$ are synthesized by reacting a compound of the formula Ia

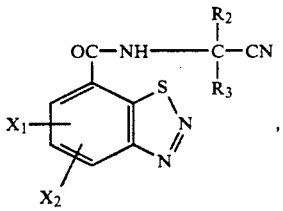
(Ia)

prepared by the above process (a) where R′ in formula IV is hydrogen, with a sulfenyl halide of the formula VII Hal—S—$R_1$ (VII)

in the presence of a base in inert solvents at temperatures of from −10° to 80° C., preferably from 0° to 50° C., where Hal is halogen, in particular chlorine, and $X_1$, $X_2$, $R_1$, $R_2$ and $R_3$ have the meanings indicated in the case of the formula I.

Compounds of the formula II in which Z is COOH can be obtained either as described in the literature (cf. J. Chem. Soc. 1971, 3997) or, advantageously, following the preparation examples given below. Acid halides which come under the formula II are prepared from the corresponding free carboxylic acids, for example with thionyl chloride, phosgene, oxalyl chloride or 1-chloro-N,N-2-trimethylpropenylamine (cf. L. Ghosez, J. Chem. Soc. Comm. 1979, 1180). Acid anhydrides which come under the formula II can be obtained for example by heating the corresponding free acid with acetic anhydride. Imidazolides and triazolides which come under the formula II are obtained from the carboxylic acids by reacting them with N,N-carbonyldiimidazole or N,N-carbonylditriazole (cf. H. A. Staab, Angew. Chemie 1964, 132).

Suitable bases are organic and inorganic bases, for example tertiary amines, such as trialkylamines (trimethylamine, triethylamine, tripropylamine etc), pyridine bases (pyridine, 4-dimethylaminopyridine, 4-pyrrolidylaminopyridine, collidine), hydroxides, carbonates and hydrogen carbonates of alkali metals and alkaline earth metals, and also alkali metal acetates.

Reaction media which are used are suitable solvents and diluents which are inert in the reaction, selected to suit the specific reaction conditions. The following are to be mentioned as examples: aliphatic and aromatic hydrocarbons, such as benzene, toluene, xylenes, petroleum ether; halogenated hydrocarbons, such as chlorobenzene, methylene chloride, ethylene chloride, dichloromethane, chloroform, carbon tetrachloride, 1,1,1-trichloroethane, tetrachloroethylene; ethers and ether-type compounds, such as dialkyl ethers (diethyl ether, diisopropyl ether, tert-butyl methyl ether etc), anisole, dioxane, tetrahydrofuran; nitriles, such as acetonitrile, propionitrile; N,N-dialkylated amides, such as dimethylformamide; ketones, such as acetone, diethyl ketone, methyl ethyl ketone; and also mixtures of such solvents with each other.

The halogenating agents used in the above-described processes are to be understood as meaning, for example, chlorine gas, sulfuryl chloride, bromine, trimethylammonium perbromide and phosphorus tribromide.

Amino compounds of the formulae III and III′ as well as sulfenyl halides of the formula VII are known or can be prepared by known methods.

The microbicidal agents for protecting plants against diseases, which are used within the scope of the invention and which contain the compounds of the formula I as active substances, are to be regarded as part of the invention.

Active ingredients of the formula I are customarily used in the form of compositions and can be applied to the plant or its environment together with other active ingredients, either simultaneously or in succession. These other active ingredients can be fertilizers, trace element supplements or other preparations which influence plant growth. However, they can also be selective herbicides, insecticides, fungicides, bactericides, nematicides, molluscicides or mixtures of a range of these preparations, if desired together with other carriers conventionally used in the art of formulation, surfactants or other additions which promote application.

Suitable carriers and additions can be solid or liquid and are the substances expedient in the art of formulation, for example natural or regenerated mineral substances, solvents, dispersants, wetting agents, tackifiers, thickeners, binders or fertilizers.

A process for applying an active ingredient of the formula I, or of an agrochemical containing at least one of these active ingredients, is application to the plant (foliar application). However, the active ingredients of the formula I can also reach the plant via the root system (soil application), by watering the habitat of the plant with a liquid preparation, or by incorporating the substances in solid form into the soil, for example in the form of granules. However, the compounds of the formula I can also be applied to seeds (coating), either by soaking the grains in a liquid preparation of the active ingredient or by coating them with a solid preparation (seed dressing). Moreover, other types of application are possible in specific cases, for example the treatment can be directed to the stems of the plants or to the buds.

For this purpose, the compounds of the formula I are used in unaltered form or, preferably, together with the adjuncts conventionally used in the art of formulation. For this purpose, they are processed in a known manner to give, for example, emulsion concentrates, spreadable pastes, directly sprayable or dilutable solutions, dilute emulsions, wettable powders, soluble powders, dusts, granules, by encapsulations for example in polymeric substances. The application methods, such as spraying, misting, atomizing, scattering, brushing on or watering, as well as the nature of the agents, are selected to suit the intended aims and the prevailing circumstances. Favourable application rates are usually 50 g to 5 kg of active substance (AS) per ha; preferably 100 g to 2 kg of AS/ha, in particular 100 g to 600 g of AS/ha.

The formulations, i.e. the agents, preparations or compositions containing the active ingredient of the formula I and if desired a solid or liquid adjunct, are prepared by intimately mixing and/or grinding the active ingredients with extenders, for example with solvents, solid carriers, and, if desired, surface-active compounds (surfactants).

The following are suitable as solvents: aromatic hydrocarbons, preferably the fractions $C_8$ to $C_{12}$, for example xylene mixtures or substituted naphthalene, phthalic esters, such as dibutyl phthalate or dioctyl phthalate, aliphatic hydrocarbons, such as cyclohexane or paraffins, alcohols and glycols as well as their ethers and esters, such as ethanol, ethylene glycol, ethylene glycol monomethyl ether or ethyl ether, ketones, such as cyclohexanone, strongly polar solvents, such as N-methyl-2-pyrrolidone, dimethyl sulfoxide or dimethylformamide; and epoxidized or unepoxidized vegetable oils, such as epoxidized coconut oil or soybean oil; or water.

Solid carriers which are generally used, for example for dusts and dispersible powders, are natural ground minerals, such as calcite, talc, kaolin, montmorillonite or attapulgite. To improve the physical properties, it is also possible to add finely divided silica or finely divided absorbent polymers. Possible granulated adsorptive granule carriers are porous types, for example pumice, crushed bricks, sepiolite or bentonite, and possible non-sorptive carrier materials are, for example, calcite or sand. Moreover, a large number of pregranulated materials of inorganic or organic nature can be used, such as, in particular, dolomite or comminuted plant residues.

Suitable surface-active compounds can be, depending on the nature of the active ingredient of the formula I to be formulated, nonionic cationic and/or anionic surfactants having good emulsifying, dispersing and wetting properties. "Surfactants" also includes surfactant mixtures.

Cationic surfactants are mainly quaternary ammonium salts which contain at least one alkyl radical having 8 to 22 C atoms as N-substituents and lower halogenated or unhalogenated alkyl radicals, benzyl radicals or lower hydroxyalkyl radicals as further substituents.

Suitable anionic surfactants can be either so-called water-soluble soaps or water-soluble synthetic surface-active compounds.

Soaps which may be mentioned are the alkali metal salts, alkaline earth metal salts or substituted or unsubstituted ammonium salts of higher fatty acids ($C_{10}$–$C_{22}$), for example the Na or K salts of oleic or stearic acid or naturally occurring fatty acid mixtures, which can be obtained from, for example, coconut oil or tallow oil.

Synthetic surfactants which can be used are, in particular, fatty alcohol sulfonates, fatty alcohol sulfates, sulfonated benzimidazole derivatives or alkylsulfonates. The fatty alcohol sulfonates or fatty alcohol sulfates are generally present as alkali metal salts, alkaline earth metal salts or substituted or unsubstituted ammonium salts and have an alkali radical having 8 to 22 C atoms.

Non-ionic surfactants are mainly polyglycol ether derivatives of aliphatic or cycloaliphatic alcohols, of saturated or unsaturated fatty acids and of alkylphenols, and they can contain 3 to 30 glycol ether groups and 8 to 20 carbon atoms in the (aliphatic) hydrocarbon radical and 6 to 18 carbon atoms in the alkyl radical of the alkylphenols.

The agents can also contain further additions, such as stabilizers, defoamers, viscosity regulators, binders, tackifiers as well as fertilizers, or other active ingredients for obtaining specific effects.

In general, the agrochemical preparations contain 0.1 to 99% by weight, in particular 0.1 to 95% by weight, of active ingredient of the formula I, 99.9 to 1% by weight, in particular 99.8 to 5% by weight, of a solid or liquid adjunct and 0 to 25% by weight, in particular 0.1 to 25% by weight, of a surfactant.

The examples below are intended to further illustrate the invention without limiting the latter.

1. PREPARATION EXAMPLES

1.1. Preparation of N-(benzo-1,2,3-thiadiazole-7-carbonyl)-2-ethoxyaminoacetonitrile (Compound 1.2)

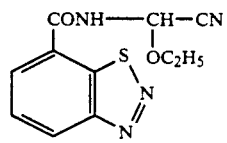

10 g of N-cyanomethylbenzo-1,2,3-thiadiazole-7-carboxamide are suspended in 140 ml of tetrahydrofuran and 140 ml of ethyl acetate, and the mixture is treated at room temperature with 5 drops of hydrobromic acid (concentrated solution in glacial acetic acid) and then 2.4 ml of bromine. The mixture is then heated slowly to 35°-40° C., during which process the reaction commences. Stirring is continued at 40° C. for 1 hour, and the mixture is then cooled to −40° C. and treated at this temperature over ½ hour with a solution of 11.4 g of ethanol and 12.0 ml of triethylamine in 10 ml of ethyl acetate, this solution being added dropwise. The mixture is then stirred until the reaction is complete, during which process the temperature rises to room temperature. For working-up, undissolved salt is filtered off, and the filtrate is evaporated and purified on silica gel (hexane/tetrahydrofuran 3:1). The resulting product is recrystallized from dichloromethane/hexane and melts at 142° C. and above with decomposition.

1.2. Preparation of N-(benzo-1,2,3-thiadiazole-7-carbonyl)-aminoacetonitrile (Intermediate)

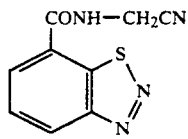

A suspension of 10.2 g of aminoacetonitrile hydrochloride in 300 ml of dichloromethane is treated at 0°-5° C., with stirring and cooling, with 31 ml of triethylamine and then 100 ml of a 1 molar solution of benzo-1,2,3-thiadiazole-7-carbonyl chloride, these substances being added dropwise. The mixture is stirred overnight at room temperature and treated with 200 ml of ice-water, the precipitate which has formed is filtered off, washed with water and dissolved in tetrahydrofuran/hexane 1:1, and the solution is filtered over a silica gel column. The filtrate is evaporated, and the residue is recrystallized from isopropanol/hexane. The product has a melting point of 237°-242° C.

1.3. Preparation of the Symmetrical Anhydride of 1,2,3-benzothiadiazole-7-carboxylic acid (Precursor)

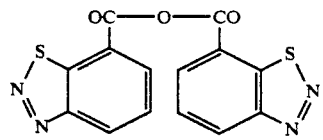

3 g of 1,2,3-benzothiadiazole-7-carboxylic acid are refluxed for 24 hours in 50 ml of acetic anhydride. The thin suspension is then evaporated in vacuo, and the solid residue is made into a slurry with ether and filtered off. This gives 4.3 g of anhydride of melting point 117°-119° C. The same compound is also obtained, for example, by heating the carboxylic acid with bis-(2-oxo-3-oxazolidinyl)-phosphinyl chloride in dry tetrahydrofuran (cf. Synthesis 1981, 616).

1.4. Preparation of 7-methoxycarbonylbenzo-1,2,3-thiadiazole (Precursor)

a) 100 g (0.35 mol) of methyl 2-benzylthio-3,5-diaminobenzoate are added in portions to 250 ml of concentrated hydrochloric acid and 110 ml of water, and the mixture is stirred at room temperature for 1.5 hours. The mixture is then cooled to −5° C. and a solution of 48.5 g (0.70 mol) of sodium nitrite in 210 ml of water is added dropwise in the course of 2.5 hours while stirring. Stirring is continued for a further 2 hours at 0° C. 190 ml of 50% hypophosphoric acid are subsequently added dropwise in the course of 2½ hours. After this, the temperature is allowed to rise to 20° C. in the course of 19 hours. The resulting product is filtered off, washed with water and dried.

For purification, the product is dissolved in ethyl acetate/methylene chloride, and the solution is filtered through silica gel, evaporated and crystallized by adding hexane. Yield: 44.4 g (65% of theory); melting 132° C.

b) 576 g (2 mol) of methyl 3,5-diamino-2-benzylthiobenzoate are dissolved in 500 ml of 1,4-dioxane, and the solution is added dropwise at 0° to 5° C., with stirring and cooling, to 5N hydrochloric acid (3 l) which has previously been introduced into the reaction vessel. The fine suspension is then cooled to −17° to −20° C. and, within 1.25 hours, treated with 294 g of sodium nitrite in 500 ml of water, this solution being added dropwise and below suspension level. While stirring is continued, the internal temperature is allowed to rise to −5° C. in the course of 1 hour and maintained for 2 hours. The mixture is then cooled to −15° C., and the suspension is added in portions and with stirring to hypophosphoric acid (1.1 l) which had been cooled to −10° to −15° C., during which process nitrogen evolves. After the addition has ended, the internal temperature is allowed to rise to room temperature in the course of 5–6 hours, the precipitate which has formed is filtered off, this is stirred with 2.5 l of methylene chloride, undissolved particles are again filtered off, and the filtrate is separated from the water. The organic phase is then dried over sodium sulfate and stirred with 300 g of silica gel, the solution is refiltered, the filter is washed with methylene chloride, and the filtrate is evaporated. Recrystallization from methanol gives a total of 244.8 g (63.1% of theory) of beige crystals of melting point 130°-133° C.

1.5. Preparation of acetonitrile N-(trichloromethylthio)-N-(benzo-1,2,3-thiadiazole-7-carbonyl)-2-thiophen-3'yl)-2amino

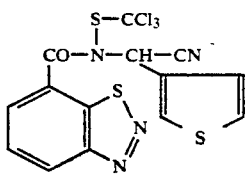

A solution of 0.43 ml of triethylamine in 3 ml of methylene chloride is added dropwise at 10° to 15° C., with stirring and cooling, to a suspension of 0.8 g of N-(benzo-1,2,3-thiadiazole-7-carbonyl)-2-thiophen-3'-yl)-2-aminoacetonitrile and 0.31 ml of perchloromethylmercaptan in 14 ml of methylene chloride. The solution which forms is stirred overnight and then treated with ice-water, and the aqueous phase is extracted using methylene chloride. The extracts are washed with water and dried over sodium sulfate. After filtration and evaporation, an oily residue remains and is chromatographed on silica gel (ethyl acetate/hexane 1:2). This gives a solid of melting point 162°–164° C.

TABLE 1

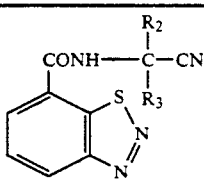

| Comp. No. | $R_2$ | $R_3$ | Physical data |
|---|---|---|---|
| 1.1 | O-Methyl | H | m.p. 169–172° C. (decomp.) |
| 1.2 | O-Ethyl | H | m.p. 142° C. (decomp.) |
| 1.3 | O-Propyl-n | H | |
| 1.4 | O-Propyl-i | H | |
| 1.5 | O-Butyl-n | H | |
| 1.6 | O-Butyl-i | H | m.p. 87–88° C. |
| 1.7 | O-Butyl-t | H | |
| 1.8 | O-Pentyl-n | H | |
| 1.9 | O-Pentyl-i | H | |
| 1.10 | O-Hexyl-n | H | m.p. 47–50° C. |
| 1.11 | O-Ethyl | Methyl | |
| 1.12 | 3-Thienyl | H | m.p. 169–172° C. |

TABLE 1-continued

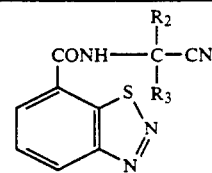

| Comp. No. | $R_2$ | $R_3$ | Physical data |
|---|---|---|---|
| 1.13 | O-Ethyl | Ethyl | |
| 1.14 | O-Butyl | Methyl | |
| 1.15 | O-Hexyl-n | Butyl-n | |
| 1.16 | S-Methyl | H | m.p. 142–145° C. |
| 1.17 | S-Ethyl | H | |
| 1.18 | S-Ethyl | Methyl | |
| 1.19 | S-Propyl-n | H | |
| 1.20 | S-Propyl-i | H | m.p. 98–101° C. |
| 1.21 | S-Hexyl-sec | Butyl-i | |
| 1.22 | Methyl | H | |
| 1.23 | Ethyl | H | |
| 1.24 | n-Propyl | H | |
| 1.25 | Butyl-i | H | |
| 1.26 | Ethyl | Methyl | |
| 1.27 | Butyl-n | Butyl-n | |
| 1.28 | Methoxymethyl | H | |
| 1.29 | Ethoxyethyl | H | |
| 1.30 | Ethoxymethyl | Methyl | |
| 1.31 | n-Propoxy-ethyl | H | |
| 1.32 | Methoxyethyl | Methyl | |
| 1.33 | Methoxymethyl | Methyl | m.p. 133–135° C. |
| 1.34 | 2-Furyl | H | |
| 1.35 | 2-Thienyl | H | |
| 1.36 | 2-Furyl | Methyl | |
| 1.37 | 2-Thienyl | Ethyl | |
| 1.38 | 3-Furyl | H | m.p. 133–135° C. |
| 1.39 | 3-Thienyl | Methyl | |
| 1.40 | 3-Furyl | Butyl-n | |
| 1.41 | 3-Thienyl | Propyl-i | |
| 1.42 | 5'-Chlorofuryl-2 | H | |
| 1.43 | 3',4',5'-Trichlorofuryl-2 | H | |
| 1.44 | 4',5'-Dichlorofuryl-2 | H | |
| 1.45 | 5'-Chlorofuryl-2 | Methyl | |
| 1.46 | 4',5'-Dichlorofuryl-2 | n-Butyl | |
| 1.47 | 2',4'-Dichlorofuryl-3 | H | |
| 1.48 | 2',4', 5'-Tribromofuryl-3 | H | |
| 1.49 | 2',4', 5'-Trichlorofuryl-3 | Methyl | |
| 1.50 | 2',5'-Difluorofuryl-3 | H | |
| 1.51 | 5'-Bromothienyl-2 | H | |
| 1.52 | 3',4',5'-Trichlorothienyl-2 | H | |
| 1.53 | 3',4',5'-Tribromothienyl-2 | n-Propyl | |
| 1.54 | 5'-Chlorothienyl-3 | H | |
| 1.55 | 2',5'-Dichlorothienyl-3 | Methyl | |
| 1.56 | 3',4',5'-Tribromothienyl-2 | H | |
| 1.57 | 4',5'-Dibromofuryl-3 | H | |
| 1.58 | 4',5'-Dichlorofuryl | H | |

TABLE 2

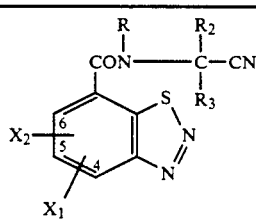

| Comp. No. | $X_1$ | $X_2$ | R | $R_2$ | $R_3$ | Physical data |
|---|---|---|---|---|---|---|
| 2.1 | H | H | Methyl | O-Methyl | H | |
| 2.2 | H | H | Methyl | O-Ethyl | H | |
| 2.3 | H | H | Butyl-n | O-Ethyl | H | |
| 2.4 | H | H | Methyl | O-Ethyl | Methyl | |
| 2.5 | H | H | Methyl | S-Ethyl | H | |
| 2.6 | H | H | Propyl-n | S-Propyl-n | H | |

TABLE 2-continued

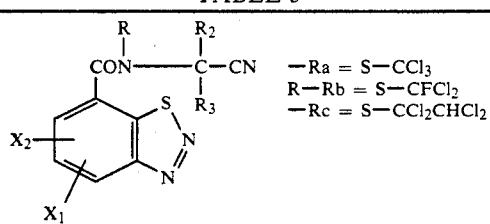

| Comp. No. | $X_1$ | $X_2$ | R | $R_2$ | $R_3$ | Physical data |
|---|---|---|---|---|---|---|
| 2.7 | H | H | Methyl | S-Butyl-n | H | |
| 2.8 | H | H | Methyl | O-Ethyl | Butyl-n | |
| 2.9 | 5-F | H | H | O-Methyl | H | |
| 2.10 | 5-F | H | H | 3-Thienyl | H | m.p. 93–95° C. |
| 2.11 | 5-F | H | H | S-Ethyl | H | |
| 2.12 | 6-F | H | H | O-Ethyl | H | |
| 2.13 | 4-F | H | H | O-Ethyl | Propyl-n | |
| 2.14 | 5-F | 6-F | H | O-Ethyl | H | |
| 2.15 | 5-J | H | H | O-Ethyl | H | |
| 2.16 | 5-Br | H | H | O-Ethyl | H | |
| 2.17 | 6-Cl | H | H | O-Ethyl | H | |
| 2.18 | 5-F | H | Methyl | O-Ethyl | H | |
| 2.19 | 5-F | H | Alkyl | O-Ethyl | H | |
| 2.20 | 4-F | 6-F | Butyl | O-Hexyl | Ethyl | |
| 2.21 | 5-F | H | 2-Pentenyl | O-Ethyl | H | |
| 2.22 | 5-F | H | H | 2'-Furyl | H | m.p. 145–147° C. |
| 2.23 | 6-F | H | H | 2'-Furyl | H | |
| 2.24 | 4-F | 6-F | H | 2'-Thienyl | H | |
| 2.25 | 5-F | H | H | 3'-Furyl | H | |
| 2.26 | 6-F | H | H | 3'-Thienyl | H | |
| 2.27 | 5-F | 6-F | Allyl | 3'-Furyl | Butyl | |
| 2.28 | 5-F | H | Methyl | 2'-Furyl | H | |
| 2.29 | 4-F | H | H | O-Ethyl | H | |
| 2.30 | 4-F | H | H | 2'-Furyl | H | |
| 2.31 | 4-F | H | H | 3'-Thienyl | H | |
| 2.32 | 5-F | 6-F | H | 3'-Thienyl | H | |

TABLE 3

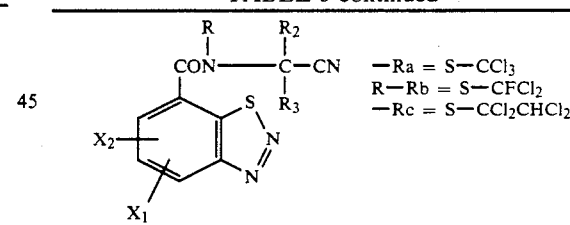

$-Ra = S-CCl_3$
$R-Rb = S-CFCl_2$
$-Rc = S-CCl_2CHCl_2$

| Comp. No. | $X_1$ | $X_2$ | R | $R_2$ | $R_3$ | Physical data |
|---|---|---|---|---|---|---|
| 3.1 | H | H | Ra | O-Ethyl | H | |
| 3.2 | H | H | Ra | O-Propyl-n | H | |
| 3.3 | 5-F | H | Ra | 2'-Furyl | H | |
| 3.4 | 6-F | H | Ra | 2'-Furyl | H | |
| 3.5 | 5-F | 6-F | Ra | 2'-Thienyl | Methyl | |
| 3.6 | H | H | Ra | 2'-Thienyl | H | |
| 3.7 | H | H | Rb | O-Ethyl | H | |
| 3.8 | H | H | Rb | O-Methyl | H | |
| 3.9 | 5-F | H | Rc | O-Ethyl | H | |
| 3.10 | 6-F | H | Rc | O-Ethyl | H | |
| 3.11 | 4-F | 6-F | Rc | O-Hexyl-n | Butyl-n | |
| 3.12 | H | H | Rc | 2'-Furyl | H | |
| 3.13 | H | H | Rc | 2'-Thienyl | H | |
| 3.14 | H | H | Rb | 2'-Furyl | H | |
| 3.15 | 5-F | H | Rb | 2'-Furyl | Ethyl | |
| 3.16 | 5-Cl | H | Ra | O-Ethyl | H | |
| 3.17 | 5-Br | H | Ra | 3'-Furyl | H | |
| 3.18 | 6-Br | H | Rb | 3'-Thienyl | H | |
| 3.19 | 5-J | H | Rc | 2'-Furyl | H | |
| 3.20 | 6-J | H | Ra | O-Ethyl | Ethyl | |
| 3.21 | H | H | Ra | 3'-Thienyl | H | m.p. 162–164° C. |

2. FORMULATION EXAMPLES OF ACTIVE INGREDIENTS OF THE FORMULA I
(%=PERCENT BY WEIGHT 2.1 Wettable powder

| | a) | b) | c) |
|---|---|---|---|
| Active ingredient from the tables | 25% | 50% | 75% |
| Na ligninsulfonate | 5% | 5% | |
| Na laurylsulfate | 3% | — | 5% |
| Na diisobutylnaphthalenesulfonate | — | 6% | 10% |
| Octylphenol polyethylene glycol ether (7-8 mol of ethylene oxide) | — | 2% | — |
| Finely divided silica | 5% | 10% | 10% |

-continued

|  | a) | b) | c) |
|---|---|---|---|
| Kaolin |  | 62% | 27% | — |

The active ingredient is mixed with the adjuncts and the mixture is ground in a suitable mill until homogeneous. This gives wettable powders which can be diluted with water to give suspensions of any desired concentration.

2.2 Emulsion concentrate

| Active ingredient from the tables | 10% |
|---|---|
| Octylphenol polyethylene glycol ether (4–5 mol of ethylene oxide) | 3% |
| Ca dodecylbenzenesulfonate | 3% |
| Castor oil polyglycol ether (35 mol of ethylene oxide) | 4% |
| Cyclohexanone | 30% |
| Xylene mixture | 50% |

Emulsions of any desired concentration can be prepared from this concentrate by diluting it with water.

2.3 Dusts

|  | a) | b) |
|---|---|---|
| Active ingredient from the tables | 5% | 8% |
| Talc | 95% | — |
| Kaolin | — | 92% |

Ready-to-use dusts are obtained by mixing the active ingredient with the carriers and grinding the mixture on a suitable mill.

2.4 Extruder Granules

| Active ingredient from the tables | 10% |
|---|---|
| Na ligninsulfonate | 2% |
| Carboxymethylcellulose | 1% |
| Kaolin | 87% |

The active ingredient is mixed with the adjuncts, and the mixture is ground and moistened with water. This mixture is extruded and then dried in a stream of air.

2.5 Coated Granules

| Active ingredient from the tables | 3% |
|---|---|
| Polyethylene glycol (MW 200) | 3% |
| Kaolin | 94% |

(MW = molecular weight)

The finely-ground active ingredient is applied uniformly in a mixer to the kaolin which has been moistened with polyethylene glycol. In this manner, dust-free coated granules are obtained.

2.6 Suspension Concentrate

| Active ingredient from the tables | 40% |
|---|---|
| Ethylene glycol | 10% |
| Nonylphenol polyethylene glycol ether (15 mol of ethylene oxide) | 6% |
| Na ligninsulfonate | 10% |
| Carboxymethylcellulose | 1% |
| 37% aqueous formaldehyde solution | 0.2% |
| Silicone oil in the form of a 75% aqueous emulsion | 0.8% |
| Water | 32% |

The finely-ground active ingredient is intimately mixed with the adjuncts. This gives a suspension concentrate, from which suspensions of any desired concentration can be prepared by diluting it with water.

3. BIOLOGICAL EXAMPLES

Example 3.1

Action Against *Colletotrichum lagenarium* on *Cucumis sativis L.* a) Cucumber plants are grown for 2 weeks and then sprayed with a spray liquor prepared from a wettable powder of the active ingredient (concentration: 200 ppm). After 48 hours, the plants are inoculated with a spore suspension ($1.5 \times 10^5$ spores/ml) of the fungus and incubated for 36 hours at a high atmospheric humidity and a temperature of 23° C. The incubation is then continued at normal atmospheric humidity and at 22° C. to 23° C.

The protective action is assessed 7–8 days after the inoculation on the basis of the fungal disease.

b) Cucumber plants are grown for 2 weeks and then treated by soil application with a spray liquor prepared from a wettable powder of the active substance (concentration: 60 ppm based on the soil volume). After 48 hours, the plants are inoculated with a spore suspension ($1.5 \times 10^5$ spores/ml) of the fungus an incubated for 36 hours at high atmospheric humidity and a temperature of 23° C. The incubation is then continued at normal atmospheric humidity and at 22° C.

The protective action is assessed 7–8 days after the inoculation on the basis of the fungal disease.

In tests a) and b), a good action is shown by compounds from Tables 1 to 3. For example, the compounds 1.2 and 1.39 reduced fungal disease to 0 to 20%. In contrast, untreated but inoculated control plants had a disease of Colletotrichum of 100%.

Example 3.2

Action Against *Phytophthora infestans* on Tomato Plants a) Tomato plants are grown for 3 weeks and then sprayed with a spray liquor prepared from a wettable powder of the active ingredient (0.02% of active substance). After 24 hours, the treated plants are inoculated with a sporangia suspension of the fungus. The assessment of fungal disease takes place after the inoculated plants have been incubated for 5 days at 90–100% relative atmospheric humidity and 20° C.

b) Tomato plants are grown for 3 weeks and the soil in which they grow is then watered with a spray liquor prepared from a wettable powder of the active ingredient (0.006% of active substance based on the soil volume). Care is taken that the spray liquor does not come in contact with the aerial parts of the plants. After 48 hours, the treated plants are inoculated with a sporangia suspension of the fungus. The assessment of fungal disease takes place after the inoculated plants have been incubated for 5 days at 90–100% relative atmospheric humidity and 20° C.

Compounds from Tables 1 to 3 show a good protective action against the Phytophthora fungus. For example, compounds 1.2 and 1.39 reduced the fungal disease to 0 to 20%. In contrast, untreated but inoculated control plants showed a disease level of Phytophthora of 100%.

Example 3.3

Action against *Plasmopara viticola* on vines a) Vine seedlings in the 4-5 leaf stage are sprayed with a spray liquor prepared from a wettable powder of the active ingredient (0.02% of active substance). After 24 hours, the treated plants are inoculated with a sporangia suspension of the fungus. The fungal disease is assessed after incubation for 6 days at 95-100% relative atmospheric humidity at 20° C.

b) Vine seedlings in the 4-5 leaf stage are inoculated with a sporangia suspension of the fungus. After incubation for 24 hours in a humid chamber at 95-100% relative atmospheric humidity and 20° C., the inoculated plants are dried and sprayed with a spray liquor prepared from a wettable powder of the active ingredient (0.06% of active substance). After the spray coating has dried on, the treated plants are transferred back to the humid chamber. The fungal disease is assessed 6 days after the inoculation.

Compounds from Tables 1 to 3 show a good protective action against *Plasmopara viticola* (disease 0-20%), for example compound 1.2. In contrast, untreated but inoculated control plants showed a disease level of Plasmopara of 100%.

Example 3:4

Action Against *Pyricularia oryzae* on Rice Plants a) Rice plants are grown for 2 weeks and then sprayed with a spray liquor prepared from a wettable powder of the active ingredient (0.02% of active substance). After 48 hours, the treated plants are inoculated with a conidia suspension of the fungus. The fungal disease is assessed after incubation for 5 days at 95-100% relative atmospheric humidity and 24° C.

b) The soil in which 2-week old rice plants are grown is watered with a spray liquor prepared from a wettable powder of the active ingredient (0.006% of active substance based on the soil volume). After this, the pots are filled with water in such a way that the basal parts of the stem of the rice plants are submerged in water. After 96 hours, the treated rice plants are inoculated with a conidia suspension of the fungus. The fungal disease is assessed after incubation of the inoculated plants for 5 days at 95-100% relative atmospheric humidity at 24° C.

When compared with untreated control plants (100% disease), rice plants which have been treated with a spray liquor containing a compound from Tables 1 to 3 as the active substance only show a low level of fungal disease. For example, compound 1.39 in test a) and compound 1.2 in test b) reduced the disease to 0 to 20%.

3:5 *Pythium altimum* on *Beta vulgaris* (sugar beet, cv. Kleinwanzleben Monogerm) and *Pythium ultimum* on *Zea mays* (maize, cv. Sweet Corn)

Test Principle
Soil fungus; local protective soil application.
Test Method

Mycelium of *Pythium altimum* is mixed with soil (500 ml of mycelium suspension per 10 liters of soil), and the fungus/soil mixture is filled into 250 ml plastic dishes. After the dishes have been incubated for 4 days at 10° C., 10 grains of the plant to be tested (maize or sugar beet) are placed in each dish. On the next day, 50 ml portions of spray solutions, prepared from 25% wettable powder and water, containing 20; 6; 2; 0.6; 0.2; 0.06 and 0.02 ppm of AS are poured into the dishes which have been prepared in this manner. After 7 days' incubation phase at 10° C. followed by 4 days' incubation phase at 22° C., the action of the test substances is evaluated by counting the emerging test plants.

Compounds from Tables 1 to 3 show a good action against *Pythium ultimum*. For example, the compound 1.2 had a protective action of over 80%.

Example 3.6

Action Against *Puccinia graminis* on Wheat a) 6 days after sowing, wheat plants are sprayed with a spray liquor prepared from a wettable powder of the active ingredient (0.02% of active substance). After 24 hours, the treated plants are inoculated with a uredospore suspension of the fungus. After incubation for 48 hours at 95-100% relative atmospheric humidity and about 20° C., the inoculated plants are placed in a greenhouse at about 22° C. The development of the rust pustules is assessed 12 days after inoculation.

b) 5 days after sowing, the soil in which wheat plants are grown is watered with a spray liquor prepared from a wettable powder of the active ingredient (0.006% of active substance based on soil volume). After 48 hours, the treated plants are inoculated with a uredospore suspension of the fungus. After incubation for 48 hours at 95-100% relative atmospheric humidity and about 20° C., the inoculated plants are placed in a greenhouse at about 22° C. The development of the rust pustules is assessed 12 days after inoculation.

Compounds from Tables 1 to 3 have a good action against fungi of the genus Puccinia. For example, compound 1.2 reduced the fungal disease to 0 to 20%. In contrast, untreated but inoculated control plants had a disease level of Puccinia of 100%.

Example 3.7

Action Against *Erysiphe graminis* on Wheat

Aestivum wheat cv. Bernina was sown at the end of September 1988 on test plots of the Experimental Station St. Aubin, Fribourg, Switzerland. In the first week of April 1989, the plants which had an average height of about 20 cm and a maximum natural disease level of *Erysiphe graminis* of 1%, were treated by spraying the foliar apparatus with an aqueous suspension of the active ingredient in a concentration of 125 g per 500 l of water per hectare.

The protective action was assessed 55 days after the treatment on the basis of the fungal disease. Compounds from Tables 1 to 3 which had been used as active ingredient showed a good action against *Erysiphe graminis*. For instance, plants which had been treated for example with compound 1.2 remained virtually free from Erysiphe disease (0-15% damage). In contrast, untreated control plants which were susceptible to the disease under the same conditions showed a disease level of 35%.

Example 3.8

Action Against *Peronospora tabacina* on Tobacco Plants

Foliar Application

Tobacco plants (age: 8 weeks) are sprayed with a formulated solution of the active ingredient (concentration: 0.02% of active substance). Four days after the treatment, the plants are inoculated with a sporangia suspension of *Peronospora tabacina* ($10^4$ sporangia/ml), placed in the dark at 25° C. under high atmospheric humidity for 20 hours and then incubated further in a normal photoperiod.

In the tests, the symptoms are assessed on the basis of the leaf area showing fungal disease.

Plants which, in the test, had been treated for example with compound 1.2, showed a disease level of 0-35%. In contrast, the control plants showed a disease level of 90 to 100%.

EXAMPLE 3.9

Action Against *Bremia lactucae* on Lettuce 80 ml portions of a test suspension containing 10 ppm of active ingredient are added to Petri dishes, each containing 100 cm³ of sterile vermiculite (exfoliated mica; Vermica AG, Bözen, CH). After this, 50 lettuce seeds are transferred to the surface of the treated vermiculite layer of each Petri dish, and the Petri dishes are incubated for about 7 days at 21° C. and photoperiod of 12 hours day/12 hours night. The plants which develop are then inoculated with a sprayed spore suspension (concentration $5 \times 10^4$ spores per ml). The Petri dishes which have been prepared in this manner are now incubated for 18-24 hours at 16° C. in the dark. The incubation is then continued under weak illumination in a 12-hour photoperiod. 2-3 weeks after the inoculation, the effect is determined by counting the inoculated seedlings and comparing them to the non-medicated control dishes.

Compounds from Tables 1 to 3 show a good action against Bremia. For example, treatment with compound 1.2 or 1.39 resulted in less than 20% of the seedlings being diseased. In contrast, the disease level in the untreated but inoculated control dishes was more than 90%.

What is claimed is:

1. A compound of the formula I

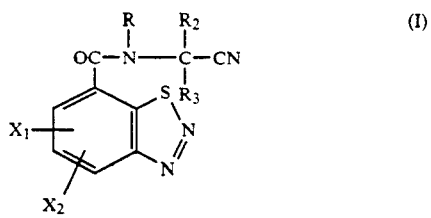

in which $X_1$ and $X_2$ independently of one another are hydrogen or 1 to 3 halogen; R is hydrogen, $C_1-C_4$alkyl, or $C_3-C_5$alkenyl; $R_2$ is $C_1-C_6$alkoxy, or is $C_1-C_6$alkylthio, or is furyl or thienyl, each of which is bonded in the 2- or 3-position; and $R_3$ is hydrogen or $C_1-C_4$alkyl.

2. A compound of claim 1 of the formula I where: $X_1$ and $X_2$ independently of one another are hydrogen or fluorine; R is hydrogen, methyl, ethyl or allyl.

3. A compound of claim 1 of the formula I where: $X_1$ and $X_2$ independently of one another are hydrogen or fluorine; R is hydrogen; $R_2$ is $C_1-C_4$alkoxy, $C_1-C_4$alkylthio, or is furyl or thienyl, each of which is bonded in the 2- or 3-position; and $R_3$ is hydrogen or $C_1-C_3$alkyl.

4. A compound of the formula I according to claim 1, where: $X_1$ and $X_2$ independently of one another are hydrogen or fluorine; R is hydrogen, methyl, ethyl or allyl; $R_2$ is $C_1-C_6$alkoxy, $C_1-C_6$alkylthio, or is furyl or thienyl, each of which is bonded in the 2- or 3-position; and $R_3$ is hydrogen or methyl.

5. A compound of the formula I according to claim 1, where: $X_1$ and $X_2$ independently of one another are hydrogen or fluorine; R is hydrogen, methyl, ethyl or allyl; $R_2$ is $C_1-C_6$alkoxy, $C_1-C_6$alkylthio, or is furyl or thienyl, each of which is bonded in the 2- or 3-position; and $R_3$ is hydrogen.

6. A compound of the formula I according to claim 1 wherein $R_2$ is ethoxy, n-propoxy, i-propoxy, n-butoxy, i-butoxy or t-butoxy.

7. A compound of the formula I according to claim 1 wherein $R_2$ is —S—($C_2H_5$), —S—(n—$C_3H_7$) or —S—(i—$C_3H_7$).

8. A compound of the formula I according to claim 1 wherein $R_2$ is 2- or 3-furyl.

9. A compound of the formula I according to claim 1 wherein $R_2$ is 2- or 3-thienyl.

10. A compound of the formula I according to claim 1, where: $X_1$ and $X_2$ independently of one another are hydrogen or fluorine; R is hydrogen; $R_2$ is $C_1-C_6$alkoxy, $C_1-C_6$alkylthio, or is furyl or thienyl, each of which is bonded in the 2- or 3-position; and $R_3$ is hydrogen.

11. A compound from the group comprising:
N-(benzo-1,2,3-thiadiazole-7-carbonyl)-2-ethoxy-2-aminoacetonitrile;
N-(benzo-1,2,3-thiadiazole-7-carbonyl)-2-methoxy-2-aminoacetonitrile;
N-(benzo-1,2,3-thiadiazole-7-carbonyl)-2-(furyl-2'yl)-2-aminoacetonitrile;
N-(benzo-1,2,3-thiadiazole-7-carbonyl)-2-(thiophen-2'yl)-2-aminoacetonitrile;
N-(benzo-1,2,3-thiadiazole-7-carbonyl)-2-(thiophen-3'yl)-2-aminoacetonitrile;
N-(5-fluorobenzo-1,2,3-thiadiazole-7-carbonyl)-2-(thiophen-3'yl)-2-aminoacetonitrile;
N-(4-fluorobenzo-1,2,3-thiadiazole-7-carbonyl)-2-(thiophen-3'yl)-2-aminoacetonitrile;
N-(benzo-1,2,3-thiadiazole-7-carbonyl)-2-(furyl-3'yl)-2-aminoacetonitrile;
N-(benzo-1,2,3-thiadiazole-7-carbonyl)-2-methylthio-2-aminoacetonitrile;
N-(benzo-1,2,3-thiadiazole-7-carbonyl)-2-isopropylthio-2-aminoacetonitrile.

12. A composition for protecting plants against attack by microorganisms, which contains, besides customary carriers and auxiliary substances, at least one compound according to claim 1 as the active ingredient.

13. A composition of claim 12 which contains at least one compound wherein $X_1$ and $X_2$ independently of one another are hydrogen or fluorine and R is hydrogen, methyl, ethyl or allyl.

14. A composition of claim 12 which contains a compound selected from the group consisting of
N-(benzo-1,2,3-thiadiazole-7-carbonyl)-2-ethoxy-2-aminoacetonitrile;
N-(benzo-1,2,3-thiadiazole-7-carbonyl)-2-methoxy-2-aminoacetonitrile;
N-(benzo-1,2,3-thiadiazole-7-carbonyl)-2-(furyl-2'yl)-2-aminoacetonitrile;
N-(benzo-1,2,3-thiadiazole-7-carbonyl-2-(thiophen-2'yl)-2-aminoacetonitrile;
N-(benzo-1,2,3-thiadiazole-7-carbonyl)-2-(thiophen-3'yl)-2-aminoacetonitrile;
N-(5-fluorobenzo-1,2,3-thiadiazole-7-carbonyl)-2-(thiophen-3'yl)-2-aminoacetonitrile;

N-(4-fluorobenzo-1,2,3-thiadiazole-7-carbonyl)-2-(thiophen-3'yl)-2-aminoacetonitrile;
N-(benzo-1,2,3-thiadiazole-7-carbonyl)-2-(furyl-3'yl)-2-aminoacetonitrile;
N-(benzo-1,2,3-thiadiazole-7-carbonyl)-2-methylthio-2-aminoacetonitrile;
N-(benzo-1,2,3-thiadiazole-7-carbonyl)-2-isopropylthio-2-aminoacetonitrile.

15. A method of protecting plants against attack by phytopathogenic microorganisms, which comprises applying, as the active ingredient, a compound according to claim 1 to the plant or its habitat.

16. A method of protecting plants against attack by phytopathogenic microorganisms, which comprises applying, as the active ingredient, a compound according to claim 11 to the plant or its habitat.

17. A method according to claim 15, in which the phytopathogenic microorganisms are fungal organisms.

* * * * *